US00PP15909P2

(12) United States Plant Patent
Whetman

(10) Patent No.: US PP15,909 P2
(45) Date of Patent: Aug. 2, 2005

(54) ***DIANTHUS* PLANT NAMED 'DEVON ELISE'**

(50) Latin Name: *Dianthus×hybrida*
Varietal Denomination: Devon Elise

(76) Inventor: John Whetman, Deer Park Farm, Chudleigh, Devon (GB), TQ13 ONH ( * ) Notice: Subject to any disclaimer, the term of this patent is extended or adjusted under 35 U.S.C. 154(b) by 84 days.

(21) Appl. No.: 10/805,620

(22) Filed: Mar. 22, 2004

(51) Int. Cl.[7] ..... A01H 5/00
(52) U.S. Cl. ..... Plt./273
(58) Field of Search ..... Plt./283, 282, 272, Plt./277, 273

(56) References Cited

U.S. PATENT DOCUMENTS

PP14,893 P2 * 6/2004 Whetman ..... Plt./283

* cited by examiner

*Primary Examiner*—Anne Marie Grunberg
*Assistant Examiner*—June Hwu

(57) ABSTRACT

A new cultivar of *Dianthus* plant named 'Devon Elise' that is characterized by compact mounding habit, blue-green foliage and prominently fragrant pink flowers with pronounced dentation of the petals. In combination these traits set 'Devon Elise' apart from all other existing varieties of *Dianthus* known to the inventor.

2 Drawing Sheets

Genus: *Dianthus*. Species: ×*hybrida*.
Denomination: Devon Elise.

BACKGROUND OF THE INVENTION

The present invention relates to a new and distinct cultivar of *Dianthus* or garden pink that is grown for use as an ornamental container plant. It is known botanically as *Dianthus×hybrida* and will be referred to hereinafter by the cultivar name 'Devon Elise'.

'Devon Elise' is the product of a breeding program started by the inventor in 1980 in a cultivated area of Houndspool, Dawlish, Devon, United Kingdom. The primary focus of the breeding program is to produce new cultivars of garden pinks that exhibit unique characteristics of flower color and form, and which, preferably, are highly and pleasantly fragrant. In addition, new varieties are selected for being well-proportioned in respect of ratio of overall height (including flower canopy) to overall width. A desirable characteristic of traditional garden pinks is the "pinking", meaning dentation, of the petal margins, from which the plant name "pink" is derived, rather than the predominant pink coloration to the blooms. The flowers of 'Devon Elise' exhibit pronounced and attractive pinking.

'Devon Elise' is a chance hybrid plant that was selected in 2000 as a single seedling from a large group (which the inventor designated as Family 9754) of open-pollinated seedlings which itself had resulted from open-pollination of a group of unnamed and unreleased plants of *Dianthus* from the inventor's large collection of *Dianthus*. The inventor is unable to identify either the male or the female parent, or to draw comparisons between 'Devon Elise' and either parent.

'Devon Elise' exhibits blue-green foliage, pink flowers and a compact mounding growth habit. The inventor's variety, *Dianthus* Plant Named 'Devon Winnie' (U.S. Plant Pat. No. 14,893) exhibits similar blue-green foliage and compact habit. However, when compared with 'Devon Winnie' the blooms of 'Devon Elise' are lighter in color, tending to pink, with markedly more pronounced dentation of the petal margins. In addition, the blooms of 'Devon Elise' are much less double in form (fewer petals in an individual bloom) than the blooms of 'Devon Winnie'.

Asexual reproduction of the new cultivar was first accomplished by the inventor in 2000 in a cultivated area of Houndspool, United Kingdom. The method of asexual propagation used was stem cuttings. Since that time the characteristics of the new cultivar have been determined stable and are reproduced true to type in successive generations by vegetative propagation.

SUMMARY OF THE INVENTION

The following traits have been repeatedly observed and represent the characteristics of the new *Dianthus* cultivar 'Devon Elise'. These traits in combination distinguish this cultivar from all other commercial varieties known to the inventor. 'Devon Elise' has not been tested under all possible conditions and phenotypic differences may be observed with variations in environmental, climatic and cultural conditions, without however any change in genotype.

1. *Dianthus* 'Devon Elise' exhibits a compact mounding growth habit.
2. *Dianthus* 'Devon Elise' exhibits fragrant pink flowers.
3. *Dianthus* 'Devon Elise' has pronounced dentation on its petal margins.
4. *Dianthus* 'Devon Elise' exhibits blue-green foliage.
5. *Dianthus* 'Devon Elise' is 15–18 cm. in height and 8–10 cm in width in a 1-liter container after 4–6 months.
6. *Dianthus* 'Devon Elise' is an evergreen perennial herb.
7. *Dianthus* 'Devon Elise' blooms from February to November.
8. *Dianthus* 'Devon Elise' is hardy to minus 15° Centigrade.

BRIEF DESCRIPTION OF THE DRAWINGS

The accompanying color drawings illustrate the overall appearance of the new *Dianthus* variety 'Devon Elise' showing colors as true as it is reasonably possible to obtain in colored reproductions of this type. Colors in the drawings may differ from the color values cited in the detailed botanical description, which accurately describe the actual colors of the new variety 'Devon Elise'.

Figure 1:
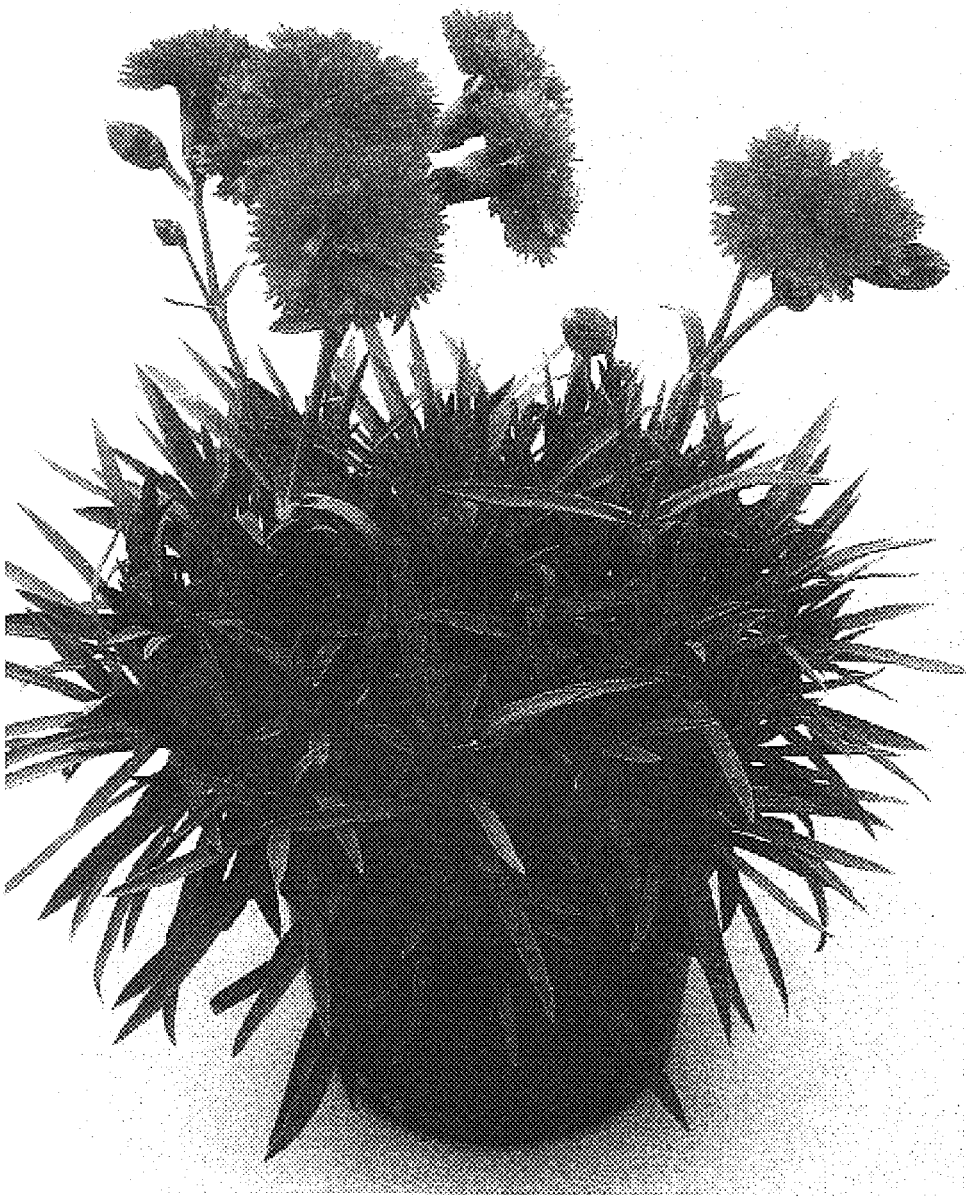

The drawing labeled as FIG. 1 illustrates an entire plant of 'Devon Elise' in flower.

Figure 2:
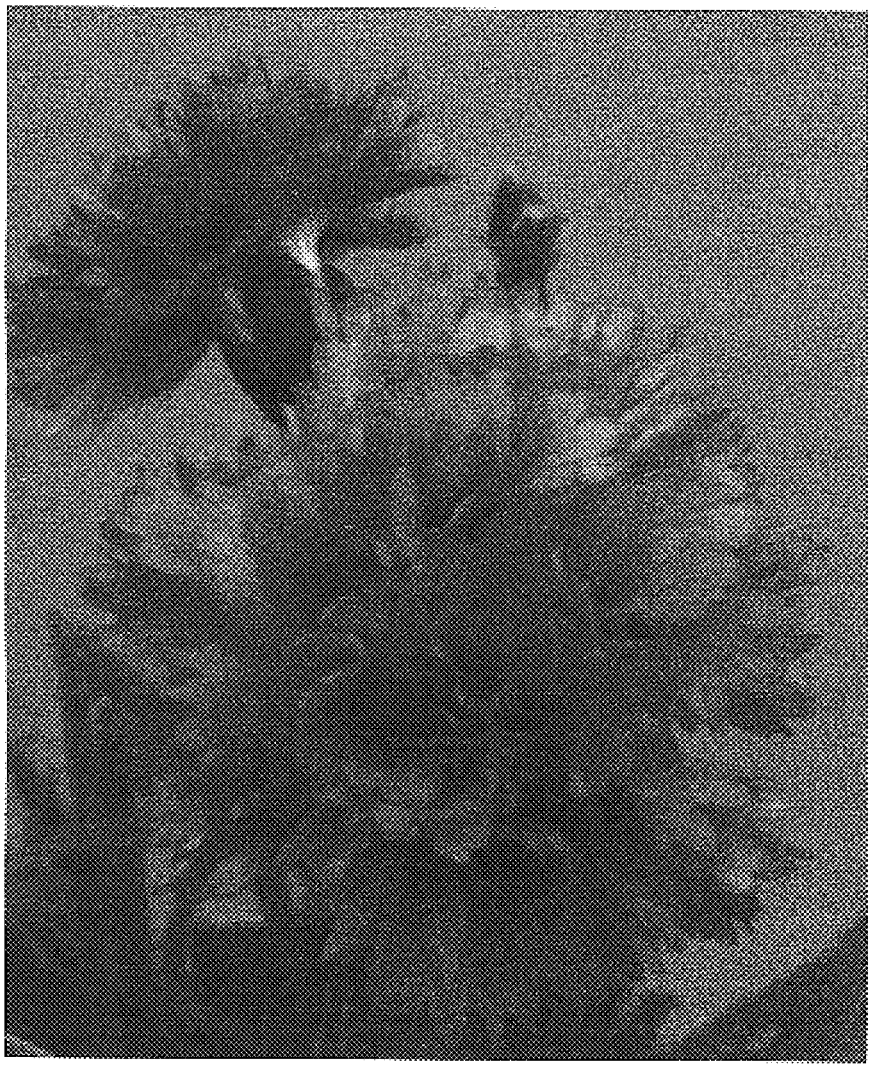

The drawing labeled as FIG. 2 illustrates is a close-up view of two typical flowers of 'Devon Elise'.

All drawings were made of nine month old grown in 1 liter containers under a cold glasshouse in Houndspool, Devon, United Kingdom. No chemicals were used to treat the plants. All drawings were made using conventional techniques and although colors may appear different from actual colors due to light reflectance they are as accurate as possible by conventional photography.

BOTANICAL DESCRIPTION OF THE PLANT

The following is a detailed description of the new cultivar 'Devon Elise'. Data was collected from plants grown in 1-liter containers under a cold glasshouse in Houndspool, Devon, United Kingdom. The color determinations are in accordance with the 2002 edition of The Royal Horticultural Society Colour Chart of The Royal Horticultural Society, London, England, except where general color terms of ordinary dictionary significance are used. No chemicals were used to treat the plants. Growing conditions are typical to other *Dianthus*.

Botanical classification: *Dianthus* 'Devon Elise'.
Species: ×*hybrida*.
Common name: Hybrid pink carnation.
Commercial classification: Hardy perennial herb.
Use: Ornamental plant for small pots and containers.
Parentage: 'Devon Elise' is a hybrid plant that resulted from the open pollination of a group of *Dianthus* seedlings named family 9754.
- *Female parent plant.*—*Dianthus* 9754.
- *Male parent plant.*—*Dianthus* 9754.

Fertility: Self-incompatible: will not normally produce fruit or seeds unless hand pollinated with another compatible clone.
Plant description:
- *Bloom period.*—February to November.
- *Plant habit.*—Compact mounding habit.
- *Plant height.*—15–18 cm. in height in a 1-liter container after 4–6 months.
- *Plant width.*—8–10 cm. in width in a 1-liter container after 4–6 months.
- *Plant hardiness.*—Hardy to minus 15° Centigrade.
- *Type.*—Perennial herb.
- *Root system.*—Fibrous.
- *Propagation.*—Propagation is accomplished using stem cuttings.
- *Cultural requirements.*—Plant in full sun, well-drained and moderately fertile soil and keep well fertilized and watered.
- *Diseases and pests.*—Susceptible to known *Dianthus* pests and disease but no other susceptibilities to pests or disease are known to the inventor.
- *Time required to produce a rooted cutting.*—2 weeks are needed to produce a rooted cutting.
- *Temperature recommended for cuttings to produce roots.*—The air temperature needed to produce a rooted cutting, is a minimum of 15° Centigrade, and a base heat of 21° Centigrade.
- *Crop time.*—4–6 months is needed to produce a finished 1-liter plant from a well-rooted cutting.

Stem:
- *Shape.*—Cylindrical.
- *Stem dimensions.*—15–18 cm. in length and 2–3 mm. in diameter.
- *Stem surface.*—Glabrous and glaucous.
- *Stem color.*—122C.
- *Branching.*—Numerous basal breaks and racemose inflorescence.
- *Internode length.*—3–5 cm. between nodes.
- *Node dimensions.*—3 mm. in diameter and 6 mm. in length.
- *Node color.*—Individual colors 122C and 144C are present.

Foliage:
- *Type.*—Evergreen.
- *Shape.*—Lanceolate.
- *Division.*—Simple.
- *Apex.*—Acute.
- *Base.*—Decurrent.
- *Venation.*—Not prominent.
- *Margins.*—Entire.
- *Attachment.*—Sheathing.
- *Arrangement.*—Opposite and spiraling on stem.
- *Surfaces* (*adaxial and abaxial*).—Glaucous.
- *Leaf dimensions.*—5–7 cm. in length and 3–5 mm. in width.
- *Leaf color* (*adaxial surfaces*).—122A.
- *Leaf color* (*abaxial surfaces*).—122A.
- *Stipules.*—2 present.
- *Stipule dimensions.*—3 mm. in width and 25 mm. in length.
- *Stipule surface.*—Glabrous, slightly ribbed.
- *Stipule color.*—122C.
- *Anthocyanin.*—Absent.
- *Fragrance.*—Absent.

Flowers:
- *Inflorescence.*—Raceme with branches.
- *Flower type.*—Double and symmetrical.
- *Flower number per stem.*—Average 3.
- *Flower shape.*—Salviform.
- *Flower dimensions* (*including calyx*).—25 mm. in length and 30 mm. in diameter.
- *Bud color.*—Each bud is a combination of colors 138A and 138C.
- *Anthocyanin.*—Absent.
- *Bud dimensions.*—15–18 mm. in length and 8–10 mm. in width.
- *Bud shape.*—Ovoid cylindrical.
- *Petals.*—Persistent double, apopetalous, overlapping.
- *Petal number.*—15–20 petals in number.
- *Petal dimensions.*—30 mm. in length and 15 mm. in width.
- *Petal margin.*—Dentate (markedly toothed 3 mm deep).
- *Petal shape.*—Obdeltoid.
- *Petal color* (*adaxial surface*).—Individual colors 54A, and 46A are each present on individual petals.
- *Petal color* (*abaxial surface*).—Individual colors 54A, 54B, and 54C are each present on individual petals.
- *Petal surfaces* (*adaxial and abaxial surfaces*).—Glabrous.

*Calyx dimensions.*—10–12 mm. in width and 15–18 mm. in length.

*Sepal color* (*adaxial surfaces*).—A combination of colors 138A and 138C.

*Sepal color* (*abaxial surfaces*).—A combination of colors 138A and 138C.

*Sepal surface.*—Glaucous.

*Sepal apex.*—Acuminate.

*Anthocyanin.*—Absent.

*Sepal number.*—5 in number.

*Fused or unfused.*—Fused.

*Epicalyx number.*—2 pairs of bracts.

*Epicalyx dimensions.*—One pair is 7 mm. in length and 5 mm. in diameter and the other pair is 5 mm. in width and 5 mm. in length.

*Epicalyx color* (*adaxial surfaces of both pairs*).—122C.

*Epicalyx color* (*abaxial surfaces of both pairs*).—122C.

*Anthocyanin.*—Absent.

*Peduncle dimensions.*—20–30 mm. in length and 1 mm. in diameter.

*Peduncle color.*—122C. weA

*Peduncle surface.*—Glaucous.

*Fragrance.*—Pronounced spicy fragrance.

*Lastingness of flower.*—10–14 days at 20° Centigrade.

Reproductive organs:

*Stamens.*—Ranges from 0–10 in number from flower to flower.

*Stamen color.*—145D.

*Stamen dimensions.*—15 mm. in length and 1 mm. in diameter.

*Anther color.*—54D.

*Anther dimensions.*—2 mm. in length and 1 mm. in diameter.

*Anther attachment.*—Dorsifixed.

*Pollen color.*—54D.

*Quantity of pollen.*—Ranges from 0 to small amount from flower to flower.

*Styles.*—Seven in number.

*Style dimensions.*—12 mm. in length and 1 mm. in width.

*Style color.*—145D.

*Stigma color.*—145D.

*Height of stigma above petals* (*at maturity*).—Exserted 3–5 mm. above petals.

*Ovary position.*—Superior.

*Ovary dimensions.*—3 mm. in height and 2 mm. in diameter.

*Ovary shape.*—Spindle shaped.

*Ovary color.*—145D.

Seed: Being self-incompatible, fruit or seeds are not produced unless hand pollinated with another compatible clone. The following data presupposes such hand pollination:

*Fruit.*—Cylindrical pod, acuminate at distil end; surface glabrous, slightly ribbed. Dimensions of fruit: 10 mm in length, 4 mm in width. Color of fruit: 122C.

*Seed.*—Irregular sphere, flattened dorso-ventrally. Dimensions of seed: 1 mm–2 mm in length, less than 0.5 mm in width. Color of seed: Black, 202A.

It is claimed:

1. A new and distinct cultivar of *Dianthus* plant named 'Devon Elise' as described and illustrated herein.

* * * * *